United States Patent [19]
Rosenthal

[11] 4,379,634
[45] Apr. 12, 1983

[54] METHOD AND DEVICE FOR DETECTING BIREFRINGENT SUBSTANCES IN LIQUIDS

[76] Inventor: Moshe Rosenthal, Bündnerstrasse 18, Basel, Switzerland, 4055

[21] Appl. No.: 835,015

[22] Filed: Sep. 20, 1977

[30] Foreign Application Priority Data

Sep. 28, 1976 [CH] Switzerland ................ 12282/76

[51] Int. Cl.³ .................. G02B 27/28; G01N 1/10; G01N 21/23
[52] U.S. Cl. .................. 356/365; 350/407; 356/246
[58] Field of Search ............ 356/114, 246; 250/225; 350/14–15, 147, 157, 159, 250, 95

[56] References Cited

U.S. PATENT DOCUMENTS

| | | | |
|---|---|---|---|
| 2,015,949 | 10/1935 | Maw | 356/246 |
| 2,056,791 | 10/1936 | Logan | 356/246 |
| 2,311,840 | 2/1943 | Land | 350/149 |
| 2,985,288 | 5/1961 | Reich | 206/363 |
| 3,104,273 | 9/1963 | Ballance | 350/159 |
| 3,208,332 | 9/1965 | Chromy | 356/30 |
| 3,582,182 | 6/1971 | Martin | 350/250 |
| 3,649,100 | 3/1972 | Kirst | 350/147 |
| 3,863,502 | 2/1975 | Elliott | 73/336 |

FOREIGN PATENT DOCUMENTS

| | | |
|---|---|---|
| 229060 | 8/1963 | Austria . |
| 1212404 | 3/1960 | France . |
| 541138 | 10/1973 | Switzerland . |
| 1157718 | 9/1969 | United Kingdom . |

OTHER PUBLICATIONS

Bausch & Lomb, "Optical Instruments in the Textile Industries", Bausch & Lomb Optical Co. 1931, p. 75.

*Primary Examiner*—William H. Punter
*Attorney, Agent, or Firm*—Wenderoth, Lind & Ponack

[57] ABSTRACT

A method and a device for detecting the presence or absence of substances having birefringent properties in liquids, particularly the detection of crystals of uric acid in samples taken by puncture from joint effusions, by placing the sample between two crossed polarizing sheets linked together about a common axis.

4 Claims, 3 Drawing Figures

METHOD AND DEVICE FOR DETECTING BIREFRINGENT SUBSTANCES IN LIQUIDS

BACKGROUND OF THE INVENTION

(1) Field of the Invention

This invention relates broadly to the field of medical diagnostics and more particularly to the uncomplicated and inexpensive bed-side diagnosis of a crystal arthritis, especially of the so-called arthritis urica.

(2) Description of the Prior Art

In many cases of inflammatory joint alterations accompanied by over-temperature, swelling and effusion formation the physician called in an emergency situation is not able to readily decide, whether the causing disease is a crystal arthritis, particularly arthritis urica, or another inflammatory or infectious arthritis. In order to determine the necessary therapeutic measure, which varies according to the result of the diagnosis, it was up till now necessary to have a sample of the joint liquid taken by puncture analysed in a specifically equipped laboratory. For the diagnosis of arthritis urica the analysis was directed to find the characteristic crystals of uric acid. Carrying or mailing the sample of the joint liquid to the laboratory and the transmission of the analysis result back causes a great time delay, which, in an unfavourable situation, e.g. if the laboratory is closed overnight, is still increased. This is extremely displeasing to the patient due to the particular painfulness of such acute joint alterations. To make things more difficult, the sample should be analysed within a few hours to permit the detection of the crystals because otherwise possibly present crystals dissolve due to a change of the pH value of the sample. In view of these reasons very often a special effort of the laboratory is requested which, however, causes substantial consumption of manpower and eventually an undesirable increase of costs. A purposeful treatment can only be made when the reason for the joint alteration is recognized through the effected analysis.

Accordingly there exists a need for a diagnostic method which permits at the bed-sided of the emergency patient the immediate distinction of a crystal arthritis from other joint diseases which may cause similar joint alterations.

SUMMARY OF THE INVENTION

It is therefore the purpose of the present invention to provide a method for detecting crystals of uric acid in samples of joint liquid taken by puncture, which method can be effected directly at the bed-side and which avoids the disadvantages caused by the analysis in a laboratory.

This is achieved by placing a small volume of the liquid to be analysed between two crossed polarizing sheets or filters directly overlying each other, and observing in transmitted light the presence or absence of light traces which contrast against the dark background of the crossed polarizers and which indicate a birefringent substance.

For performing this method a device is suitable which comprises two polarizing sheets or filters which are linked together about a common axis in such a way that their directions of polarization are crossed when the sheets or filters are directly overlying each other.

Other objects, advantages and capabilities of the present invention will become apparent from the following detailed description taken in conjunction with the accompanying drawings, showing only a preferred embodiment of the invention.

DESCRIPTION OF PREFERRED EMBODIMENTS

Figure 1:
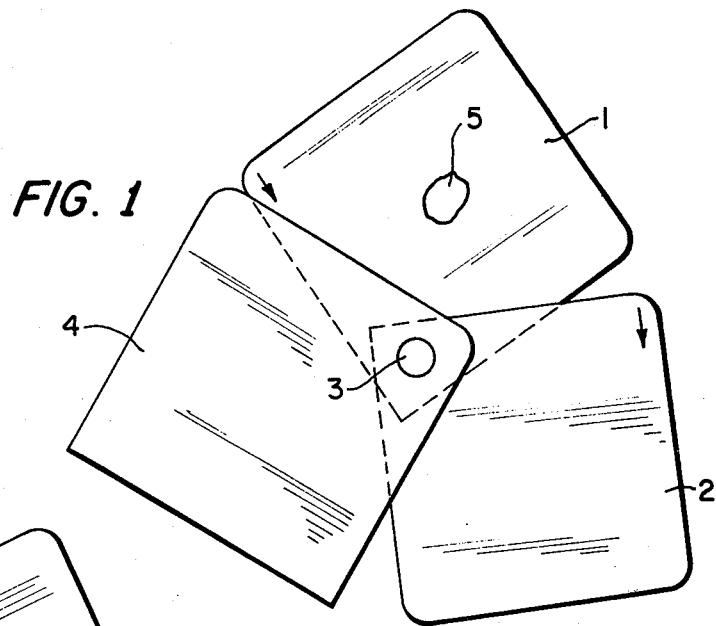
FIG. 1 shows a device for detecting birefringent substances in liquid samples in an open configuration.
Figure 2:
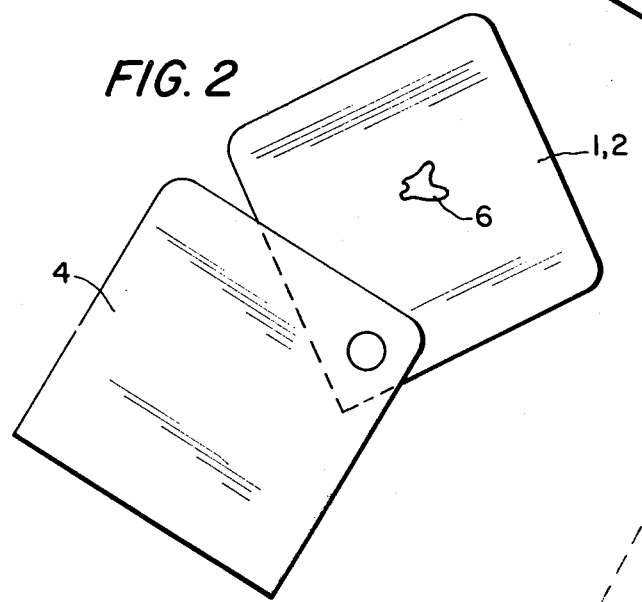
FIG. 2 shows the same device with the polarizers brought to coverage.

The device shown in FIGS. 1 and 2 comprises two polarizers 1,2 the directions of polarization of which are indicated by the arrows in one of their respective corners. In the present example the two polarizing sheets are square-shaped with rounded corners and they have a side length of about 50 millimeters. This dimension has proven to be practical. It is self-evident however, that other dimensions or forms are possible, e.g. circular etc., as long as a practical size is not exceeded.

Each of the two polarizer sheets 1,2 has at one of its corners a hole through which they are connected to each other by means of a rivet 3. The rivet 3 constitutes an axis about which the two polarizers can be displaced or rotated against each other in a fan-like fashion. The holes for receiving the rivet 3 are located relative to the polarizing directions such that these polarizing directions are crossed when the polarizing sheets 1 and 2 are exactly overlying each other.

As a material for the polarizing sheets, as an example, polarizing plastic foil has proven to be suitable. Foils of this type are commercially available from the Polaroid Corporation. For the present embodiment foils of at thickness of 0.1, 0.3 and 0.8 millimeters have been employed. One may use also other sizes whereby the lower limit due to the necessary mechanical strength is about 0.1 millimeter, whereas the upper limit is mainly determined by the price and may be about 1.0 millimeter.

The rivet 3 serves at the same time as a connector between the two polarizers and a protective cover 4. The protective cover consists of a flexible plastic foil, the dimension of which being such that when folded once it is about the same size or a little larger than the polarizers 1,2. In the assembled state the two polarizers are situated between the two halfs of the folded plastic cover 4 and they may be pushed into the cover or moved out in a fan-like manner to be ready for the intended detection.

For instance, to detect crystals of uric acid in a sample taken from a joint effusion the two polarizers 1 and 2 are moved out of the protective cover in a fan-like manner as shown in FIG. 1. A drop 5 of the joint liquid to be analysed is placed on the lower polarizer 1. Then, the other polarizer 2 is moved on top of the first polarizer and they are brought to exact coverage. The two polarizers are pressed against each other and held against a light source or incident daylight.

If the sample does not contain any birefringent crystals the entire area is uniformly dark due to the crossed polarisation directions. If the sample, however, contains birefringent crystals a light spot 6 appears at the place where such crystals are. For the inspecting physician this means that the disease causing the joint effusion is clearly a crystal arthritis. Thus he can take the appropriate therapeutic measures. Practically no time is lost between taking the sample of the joint liquid by puncture and the diagnosis result.

Since the described device is intended for repeated use, all its elements should be made of materials which allow cleansing with water. It may also be an advantage to choose the materials such that sterilisation is possible for the case that the originating disease is an infectuous arthritis.

In order to facilitate the cleaning or the sterilisation operation the rivet 3 may be replaced by an easily detachable screw or a connecting element of the pressbutton type. In this way polarizers 1,2 and protecting cover 4 may be disengaged.

Another possibility consists in designing the device as a disposable article for one single use only. In this case for economic reasons the polarizing foils will be chosen as thin as possible and the protective cover may be omitted.

Figure 3:
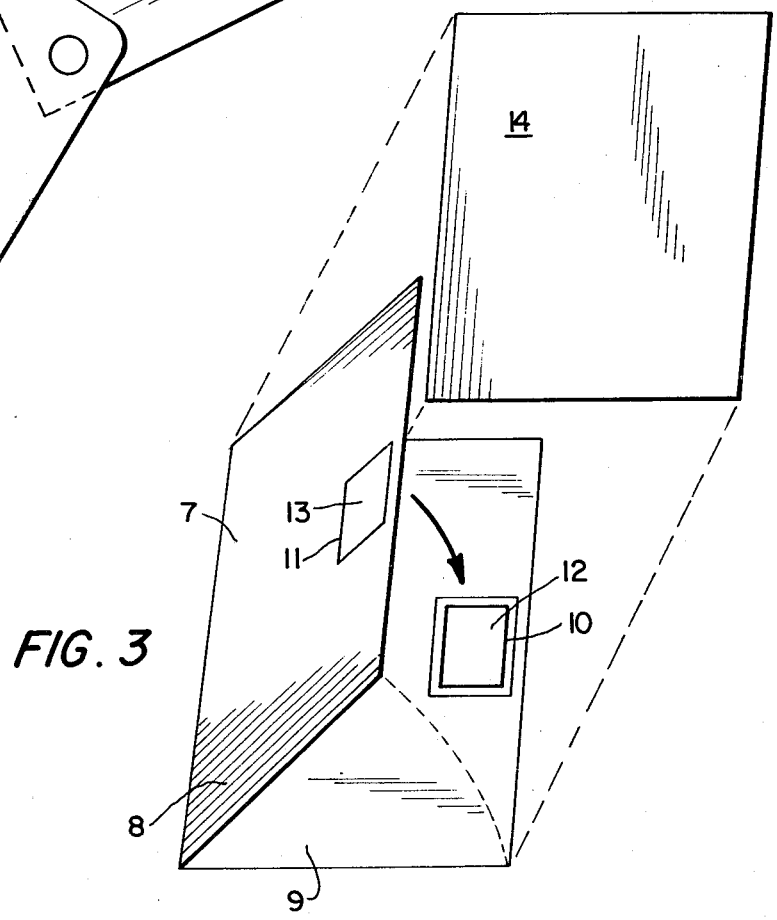
FIG. 3 shows an alternative device which is particularly useful for a single determination only and for simultaneous documentation

The device shown in FIG. 3 is particularly suitable for being used once and for subsequent documentation of the patient information and the diagnosis.

The device consists of a cardboard 7 which is folded once along its middle line and which serves as a carrier for two polarizing foils 12 and 13. The two halves 8,9 of the cardboard 7 each have a rectangular piece cut out (10,11). The cut-outs are situated such that they overlie and cover each other exactly when the two halves of the cardboard are folded together. The polarizing foils 12,13 are mounted in the rectangular cut-outs. The pieces of foil are slightly larger than the cut-outs and are glued to the cardboard along their extending edges.

Variations of this embodiment are, of course, possible. Thus the folded card 7 serving as a carrier may be made of another material instead of cardboard, e.g. of a suitable opaque, transparent or translucent plastic material. Moreover it is not absolutely necessary that the carrier or support is formed by a folded sheet. It is also possible to connect two separate sheets along one of their edges, e.g. by means of an adhesive tape etc. The cut-outs 10,11 may also have a square, circular or other shape instead of a rectangular shape. It is also not absolutely indispensable that the two cut-outs exactly cover each other but it is preferable. For the attachment of the foils in or over the cut-outs any other method is acceptable instead of gluing, such as welding in case of the use of a plastic foil as a carrier, etc.

The polarizing foils 12,13 are mounted such that their directions of polarization are perpendicular to each other when the two halves of the carrier are folded together.

In the present embodiment an additional inserted sheet 14 is provided which has a size of about one half the size of the cardboard 7. On this inserted sheet the inspecting physician may make notes on the patient, the inspection and the diagnosis.

Prior to use the inserted sheet 14 lies between the halves of the cardboard sheet 7. In order to perform a determination the inserted sheet is removed from the cardboard.

A drop of the liquid to be analysed, for example a sample of joint liquid taken by puncture, is deposited on the lower polarizing foil. The cardboard sheet is folded together such that the two polarizing foils cover each other with the drop in between. The two parts of the cardboard sheet and thus the polarizing foils are pressed together and held against incident light for observation.

The determination of whether the drop of sample liquid contains birefringent crystals is effected in the same manner as with the previously described embodiment.

It is self-evident that the notes about the patient and the diagnosis may also be put directly on the cardboard sheet itself. In this case the cardboard sheet may be provided with an appropriate printed form, e.g. on its front side.

It is equally possible to use a copying set consisting of several sheets instead of a single inserted sheet.

After the determination has been effected and the result has been noted the inserted sheet as well as the used device itself can be filed for documentation.

It may be advantageous to connect the inserted sheet with the cardboard sheet in such a way that it has to be torn out, e.g. along a perforation line. The determination cannot be effected before the inserted sheet is removed. In this way a device with a still fixed inserted sheet can be identified as being unused. An inadvertent double use, which could result in wrong results is thus eliminated.

What I claim is:

1. Method for determination of birefringent solid particles or crystals in liquids, said method comprising placing a small amount of the liquid to be analysed between two polarizing sheets, moving said two sheets relative to each other to a relative position where they directly overlie each other with crossed directions of polarization, pressing said two sheets against each other, and observing in transmitted light the presence or absence of light traces contrasting against the dark background of the crossed polarizers, the presence of which traces indicating the presence of birefringent solid particles or crystals in said liquid.

2. Device for determination of birefringent solid particles or crystals in liquids, said device comprising two polarizing sheets linked together about a common axis in a manner such that said two sheets are movable about said axis to positions whereat said sheets directly overlie each other, the directions of polarization of said sheets being crossed when said sheets are in said positions, and such that said two sheets may be pressed against each other when in said positions, wherein said axis extends substantially transverse to the planes of said two polarizing sheets and connects said sheets adjacent the peripheries thereof, such that said sheets can be moved relative to one another in a fan-like manner.

3. A method as claimed in claim 1, wherein said two sheets are connected to each other about a common axis extending substantially transverse to the planes of said sheets, and said step of moving comprises rotating said sheets about said axis.

4. A method as claimed in claim 1, wherein said two sheets are movable with respect to each other about a common axis extending substantially parallel to the planes of said sheets, and said step of moving comprises pivoting said sheets about said axis.

* * * * *